United States Patent [19]
Frentzen et al.

[11] Patent Number: 6,111,099
[45] Date of Patent: Aug. 29, 2000

[54] PROCESS FOR THE RECOVERY OF CAPROLACTAM FROM WASTE CONTAINING NYLON

[75] Inventors: Yvonne H Frentzen, Venlo, Netherlands; Marcellinus P. G. Thijert, Augusta, Ga.; Rudolf L. Zwart, Sittard, Netherlands

[73] Assignee: DSM N.V., Heerlen, Netherlands

[21] Appl. No.: 09/005,512

[22] Filed: Jan. 12, 1998

Related U.S. Application Data

[63] Continuation of application No. PCT/NL96/00283, Jul. 11, 1996.

[30] Foreign Application Priority Data

Jul. 12, 1995 [NL] Netherlands ............... 1000781

[51] Int. Cl.[7] .................................................. C07D 201/16
[52] U.S. Cl. ............................................................ 540/540
[58] Field of Search .............................................. 540/540

[56] References Cited

U.S. PATENT DOCUMENTS

| | | | |
|---|---|---|---|
| 3,912,721 | 10/1975 | Mattone et al. | 260/239.3 |
| 4,013,640 | 3/1977 | Somekh | 260/239.3 |
| 5,359,062 | 10/1994 | Fuchs | 540/540 |
| 5,360,905 | 11/1994 | Fuchs | 540/540 |
| 5,457,197 | 10/1995 | Sifniades | 540/540 |
| 5,656,757 | 8/1997 | Jenczewski et al. | 540/540 |
| 5,681,952 | 10/1997 | Sifniades et al. | 540/540 |

FOREIGN PATENT DOCUMENTS

| | | |
|---|---|---|
| 0 568 882 A1 | 11/1993 | European Pat. Off. . |
| 0 570 843 A3 | 11/1993 | European Pat. Off. . |
| 0 627 417 A1 | 12/1994 | European Pat. Off. . |
| 0 676 394 A1 | 10/1995 | European Pat. Off. . |
| 2 332 973 | 1/1974 | Germany . |

OTHER PUBLICATIONS

Tsvetkov, V.F., Selection of an extractant for caprolactam extraction form sulfuric acid solutions, Chemical Abstracts, Chemistry of Synthetic High Polymers, Sep. 17, 1984, vol. 101, No. 12 (Abstract 101:91474a).

Soto, et al., p–Nonyl–Phenol: An Estrogenic Xenobiotic Released from "Modified" Polystyrene, Environmental Health Perspectives, 1991, vol. 92, pp. 167–173.

Heath, Caprolactam From Toluene–Without Ammonium Sulfate, Chemical Engineering, vol. 81, No. 15, Jul. 22, 1974, pp. 70–71.

Kikic, et al., Separation of Caprolactam from alkyl phenols . . . , Advances in Separation Science, Trieste 1978, pp. 243–255.

*Primary Examiner*—Richard L. Raymond
*Assistant Examiner*—Bruck Kifle
*Attorney, Agent, or Firm*—Pillsbury Madison & Sutro Intellectual Property Group

[57] ABSTRACT

A process for depolymerizing nylon 6 and recovering caprolactam from the depolymerized products by extraction with alkyl phenolic compounds. Process steps include (a) treating a first mixture comprising nylon 6 with water at a temperature between about 200° C. and about 400° C. to yield a second mixture comprising depolymerized nylon 6 components, wherein the second mixture contains caprolactam at a concentration between about 5 wt. % and about 35 wt. %; (b) optionally, separating insoluble material from the second mixture; (c) extracting the second mixture with an extraction agent to yield an aqueous raffinate third mixture and an organic phase fourth mixture comprising caprolactam and the extraction agent, wherein the extraction agent is an alkyl phenol having a boiling point higher than that of the caprolactam; (d) recovering caprolactam from the organic phase fourth mixture by distillation; (e) recycling the aqueous raffinate third mixture to step (a).

10 Claims, No Drawings

PROCESS FOR THE RECOVERY OF CAPROLACTAM FROM WASTE CONTAINING NYLON

This is a continuation of International Appln. No. PCT/NL96/00283 filed Jul. 11, 1996 which designated the U.S.

BACKGROUND OF THE INVENTION

1. Field of the Invention

The present invention relates to a process for the recovery of caprolactam from nylon-containing waste which has been converted to depolymerization products. After depolymerization, caprolactam is extracted from depolymerized products with use of alkyl phenolic type solvents.

2. Description of Related Art

Nylon containing waste, especially waste carpet simultaneously represents not only an environmental problem but also a potential source of value if useful materials can be recovered from it. For example, much waste carpet contains significant amounts of nylon, and in particular, nylon 6 or polycaprolactam. Processes for depolymerization of the waste nylon 6 to its valuable monomer, caprolactam, have been developed. Improvements in such processes, however, are still needed.

Nylon 6 depolymerization is usually effected in the presence of water. Although caprolactam is formed by depolymerization, the depolymerization reaction is an equilibrium reaction and at least some, and often significant, amounts of cyclic and linear caprolactam oligomers also form. Pure caprolactam, however, is ultimately desirable, but purification processes to separate the oligomers from the monomer can be cumbersome and expensive. Once separated from monomer, caprolactam oligomers can be recycled for further depolymerization. Therefore, despite the utility of known nylon 6 depolymerization and caprolactam purification processes, improved methods are still needed to make such processes economically attractive. Ideally, complete elimination of one or more purification steps is desirable.

Extraction is a method to separate caprolactam from complex mixtures resulting from nylon 6 waste depolymerization. For extraction to be effective, the solubilities of the different components must be carefully considered.

U.S. Pat. No. 5,359,062 discloses that nylon 6 can be depolymerized in the presence of water and alkali metal hydroxide to yield caprolactam- and oligomer-containing aqueous solutions. Following depolymerization, caprolactam can be separated by distillation or extraction. In order to have an economically attractive process it is essential to separate the oligomer from monomeric caprolactam and to recycle the oligomers.

The distillation route, however, suffers from the drawback that the distillation residue may not be readily recyclable because of tar formation. Other circumstances hindering the recycling of the residue include repolymerization and solidification of the oligomers. The extraction route suffers from, among other things, the need for large amounts of extraction agent. For example, more than twice the amount of extraction agent compared to the amount of caprolactam-containing aqueous solution may be needed. Moreover, although this patent disclosure mentions oligomer formation and separation, it does not disclose or suggest solutions to the particular problem of removing cyclic or linear oligomers from caprolactam. The extraction agents disclosed in U.S. Pat. No. 5,359,062 include benzene, toluene, and xylene, all of which are relatively low-boiling solvents compared to caprolactam. During extraction, these solvents extract not only caprolactam but also cyclic caprolactam oligomers. After extraction, these solvents can be removed from the caprolactam by distillation. An additional distillation step, however, is then needed to separate caprolactam from the cyclic oligomers. Hence, following the caprolactam extraction step, two distillations are still required to obtain the pure caprolactam.

U.S. Pat. No. 4,013,640 discloses an amide purification process which includes purification of caprolactam. This patent, however, also fails to address the problem of removing oligomers, and in particular, cyclic oligomers from caprolactam. Moreover, this patent publication also fails to disclose caprolactam purification processes which follow depolymerization of nylon 6. Rather, it discloses extraction of caprolactam from unspecified industrial waste waters. The disclosed impurities in these wastes are not impurities of similar chemical character as the amide to be purified. Extraction is effected with use of alkyl phenolic type solvents having boiling points higher than caprolactam. The extraction step is followed by vacuum distillation of the extract to obtain caprolactam. This distillation may be hampered by the presence of oligomers. U.S. Pat. No. 4,013,640, however, neither suggests nor discloses that alkyl phenolic extraction agents would be useful to separate caprolactam oligomers from caprolactam.

SUMMARY OF THE INVENTION

Objects of the present invention include improving the efficiency of the caprolactam purification procedure following depolymerization of nylon, and in particular, nylon 6.

An additional object is to improve the ability to separate oligomers from caprolactam.

An additional object is to improve the economics of waste carpet recycling.

These and other objects are achieved by a process comprising the combination of steps of:

a) treating a first mixture comprising nylon 6 with water at a temperature between about 200° C. and about 400° C. to yield a second mixture comprising depolymerized nylon 6 components, wherein the second mixture contains caprolactam at a concentration between about 5 wt. % and about 35 wt. %;

b) optionally, separating insoluble material from the second mixture;

c) extracting the second mixture with an extraction agent to yield an aqueous raffinate third mixture and an organic phase fourth mixture comprising caprolactam and the extraction agent, wherein the extraction agent is an alkyl phenol having a boiling point higher than that of the caprolactam;

d) recovering caprolactam from the organic phase fourth mixture by distillation;

e) recycling the aqueous raffinate third mixture to step (a).

Advantages of the present inventions include improved efficiency in the caprolactam purification process, particularly with respect to separation of oligomers from the caprolactam.

DETAILED DESCRIPTION OF THE INVENTION

The present invention is effective in treating waste mixtures comprising nylon 6. In addition to nylon 6, other types of polymers, nylons, and polyamides which can be in the waste mixture include polyproplene, polyethyleneterephtalate, jute, SBR, wool, cotton, nylon 66. The composition of the waste mixture is not strictly limited so long as the advantages of the present invention can be achieved. The waste mixture, for example, can be relatively homogeneous or heterogeneous. In particular, the present inventions can be used to process industrial and post-consumer carpet waste. The carpet is preferably first comminuted mechanically by, for example, grinding, chopping, tearing, or cutting by means of knives and/or shears. The greater part of the non-polyamide components of the carpet can contain, for example, unfilled latex, latex filled with $CaCO_3$, jute, and polypropylene. Such non-polyamide components can be separated from the polyamide or nylon 6 component of the carpet in one or more separation steps before depolymerization treatment at elevated temperatures. Alternatively, carpet pieces also can be supplied directly to the reactor for depolymerization.

The inventions yield good results with between about 5 wt. % and about 50 wt. % of polyamide in the reactor besides other components (as earlier mentioned).

The nylon 6 containing waste mixture is treated with water at elevated temperature and, if desired, at elevated pressure to effect depolymerization of nylon 6.

In general, depolymerization is effected with a quantity of water so that, after depolymerization, an aqueous solution is obtained containing between about 5 wt. % to about 35 wt. %, and preferably, less than about 25 wt. % of caprolactam relative to the amount of water.

The temperature at which the depolymerization process can be performed is not particularly limited, but is in general, between about 200° C. and about 400° C., and preferably, between about 250° C. and about 350° C.

The depolymerization pressure also is not particularly limited but can be, in general, less than about 200 bar, and preferably, less than about 130 bar. For example, pressures are contemplated of about 100 bar, or 10 MPas, at about 300° C.

When depolymerization is carried out for about 1 hour under these conditions, a virtual equilibrium is reached, and the caprolactam:oligomer ratio is generally about 4:1 by weight. The invention, however, also contemplates amounts of oligomers up to 35 wt. % with respect to caprolactam. The amounts of oligomer formation make recycling essential for economic reasons.

Depolymerization is preferably carried out without a catalyst or accelerator. In order to control the reaction rate and the selectivity, however, depolymerization catalysts or accelerators can also be used if desired. Suitable catalysts include Lewis acids such as, for example, $Al_2O_3$, $SiO_2$; and Brønsted acids such as, for example, $H_3PO_4$, paratoluene sulfonic acid, formic acid, $H_3BO_3$, or salts thereof like, for example, ammonium salts. Base catalysts can also be used such as, for example, NaOH, KOH or $Na_2CO_3$. These compounds are optionally present in an amount of about 0.1 wt. % to about 20 wt. %, and preferably, between about 0.1 wt. % to about 5 wt. % relative to the polyamide.

Following depolymerization, a mixture comprising caprolactam and other depolymerized products such as linear and cyclic oligomers is formed. The mixture will usually contain insoluble material, although alternatively, no substantial amounts of insoluble material will be present in some cases if insoluble materials were removed before depolymerization. Insoluble material includes jute, $CaCO_3$, polypropylene.

Before the extraction step, measures are preferably taken so that virtually no solid, undissolved waste is present in the aqueous solution. This can be achieved by methods known to those skilled in the art including filtration or centrifugation. Alternatively, separation can be effected by separating out the aqueous solution with caprolactam as an aerosol. This means that depolymerization step (a) and separation step (b) can be separate or simultaneous steps.

The caprolactam extraction step is effected with an alkyl phenolic type extraction agent. The amount of alkyl phenol is not particularly limited provided that the advantages of the present invention can be achieved. The upper limit, for example, is not believed critical but depends on process economy. In general, the amount of alkyl phenol will be less than about 1½ times the volume amount of aqueous solution. By preference, about 5 to about 100 vol. % of alkyl phenol relative to the amount of aqueous solution is used. Very good results are achieved if about 30 to about 80 vol. % of alkyl phenol relative to the amount of aqueous solution is used.

The extraction agent can be an alkyl phenol having a boiling point higher than the boiling point of caprolactam, which is 272° C. at 1 bar. Alkyl phenols have a high boiling point at atmospheric pressure. Therefore, boiling points are advantageously compared at reduced pressures of, for example, 1.3 kPa (10 mm Hg). Caprolactam has a boiling point of 140° C. at 10 mm Hg, while dodecyl phenol, for example, has a boiling point of 190° C. at that pressure. By preference, the boiling point of the alkyl phenol is more than about 5° C., and in particular, more than about 15° C. higher than the caprolactam boiling point at 1.3 kPa (10 mm Hg). The upper limit to the boiling point of the alkyl phenol is about 400° C. The alkyl phenol preferably is non-azeotropic with caprolactam. Mixtures of alkyl phenol can be used.

The alkyl component of the alkyl phenol can be, for example, a $C_6$–$C_{25}$ alkyl component, and preferably, a $C_9$–$C_{15}$ alkyl component. Alternatively, the alkyl component can consist of one or more alkyl groups which together contain 6 or more carbon atoms. The alkyl component preferably consists of an aliphatic or aromatic hydrocarbon, and in particular, aliphatic hydrocarbon. Examples of specific alkyl phenolic compounds include dodecyl phenol, octyl phenol, nonyl phenol, n-hexyl phenol, 2,4-diisobutyl phenol, 2-methyl-4,6-di-tert-butyl phenol, 3-ethyl-4,6-di-tert-butyl phenol, 2,4,6-tri-tert-butyl phenol, and mixtures of any thereof. U.S. Pat. No. 4,013,640 discloses additional alkyl phenols, the complete disclosure of which is hereby incorporated by reference.

The extraction step is, in general, carried out at a temperature which is higher than the melting point of the alkyl phenol. The temperature of extraction can be generally between about 50° C. and about 220° C., and preferably, between about 70° C. and about 170° C. Generally, the extraction temperature is selected so that the maximum amount of solid non-nylon products can be separated out. If, for example, waste polypropylene is present in the mixture to be extracted, the temperature is preferably lower than the melting point of the waste polypropylene. Therefore, in this case, the extraction temperature is preferably lower than about 130° C.

The pressure during the extraction step is not generally critical and can be, for example, between about 1 bar and about 20 bar, and preferably, between about 1 bar and about 5 bar.

The extraction step yields a caprolactam-containing organic phase which, in general, contains up to 50 wt. % caprolactam and between about 0 and about 15 wt. % water.

The amount of cyclic oligomers in the organic phase extract is generally less than about 10 wt. %, and preferably less than about 5 wt. %, and the amount of linear oligomers is generally less than about 1 wt. %, and preferably less than about 0.1 wt. %.

After extraction and removal of the extraction agent, an aqueous raffinate mixture remains. Even after the greater amount of the caprolactam has been extracted out, however, the aqueous solution still contains some caprolactam. In general, the concentration of remaining caprolactam is less than about 2 wt. %, and preferably, less than about 1 wt. %. After extraction, the aqueous solution in addition still contains caprolactam oligomers, including mainly linear oligomers, soluble polymers, or mixtures thereof. Oligomers and polymers of caprolactam may partially precipitate during extraction of caprolactam resulting in slurry formation. If desired, additional water can be added to the slurry in order to form a solution again. The aqueous solution or slurry is recycled to depolymerization step (a). If the raffinate still contains insoluble solid, non-nylon waste, that waste will preferably will be separated out beforehand by means of filtration.

After extraction, caprolactam and residual water can be distilled out of the organic phase. After this distillation, the alkyl phenol containing cyclic oligomers can be used again in other extraction operations, if required after purification of the extraction agent. In this distillation step, the required purification of caprolactam is partially achieved directly because all heavy components remain behind in the alkyl phenol.

The liquid caprolactam, after distillation out of the alkyl phenol, which contains between about 5 to about 50 wt. % water is subsequently further purified and/or concentrated. This results in caprolactam of a quality that is comparable with that of virgin caprolactam.

In one preferred embodiment, the purification of the extracted and distilled caprolactam comprises the following steps:

1) ion exchange
2) hydrogenation
3) distilling out water and other light components
4) distilling out caprolactam.

The order of the ion exchange step (1) and hydrogenation step (2) can be reversed if desired. This purification procedure results in caprolactam of very good quality.

In a second preferred embodiment, the purification of the distilled caprolactam is achieved by crystallization in a process of concentrating. The crystallized caprolactam resulting from concentrating is generally sufficiently pure to be used directly. After crystallization, it may be necessary to purify the mother liquor by, for example, recycling it to the aqueous solution before the extraction with the alkyl phenol. The mother liquor can be purified for example by means of destillation.

The inventions will now be elucidated by means of the following non-restrictive examples.

EXAMPLES

Example 1

46.4 kg of water phase was added to 16.8 kg of carpet pieces having a size of about 1–5 cm$^2$ (38 wt. % nylon 6) to yield a heterogeneous mixture. The water phase was obtained from the extraction (the raffinate mixture) and contained about 3.4 wt. % of linear oligomers of nylon 6. Depolymerization of nylon 6 was carried out in a depolymerization reactor at a temperature of 300° C. and at a pressure of 100 bar for 1 hour to yield a slurry mixture. The resulting slurry was cooled and depressurized, so that part of the water was evaporated (100° C., 1 bar). After this, solid particles were removed from the slurry by filtration at a temperature of 100° C. to yield a filtered mixture. This mixture contained approximately 31 kg of water, 6.3 kg of caprolactam and 1.6 kg of caprolactam oligomers. The oligomers were 1.44 kg linear oligomers and 0.16 kg cyclic oligomers.

This mixture was extracted with 25 kg of dodecyl phenol at 100° C. so that virtually all caprolactam and cyclic oligomers and 1.3 kg of water were present in the resultant organic phase mixture. The remaining raffinate mixture was fed back to the hydrolysis section of the depolymerization reactor. This raffinate contained the linear oligomers that were present in the water phase after depolymerization and extraction.

Caprolactam and water were distilled out of the dodecyl phenol which resulted in a caprolactam flow containing 18 wt. % of water. This flow (1 bar, 55° C.) was treated with an ion exchanger and then subjected to hydrogenation. The water and light components were distilled out at 0.2 bar and 56° C., after which pure caprolactam was recovered through distillation at 5 mbar and 116° C.

While the present invention has been illustrated by means of several preferred embodiments, one of ordinary skill in the art will recognize that changes, modifications, and improvements can be made while still remaining within the scope and spirit of the present invention.

All references disclosed herein are hereby incorporated by reference.

We claim:

1. Process for the recovery of caprolactam from waste which contains nylon 6 by
   a) treating a first mixture comprising waste which comprises nylon 6 with water at a temperature between 200° C. and 400° C. to yield a second mixture comprising depolymerized nylon 6 components,
   b) optionally, separating the second mixture from any insoluble (carpet) waste that is present,
   c) subjecting said second mixture to an extraction with an organic extraction agent to yield an aqueous raffinate third mixture and an organic phase fourth mixture comprising caprolactam and said extraction agent,
   d) recovering the caprolactam from said organic phase fourth mixture by distillation,
   e) recycling said aqueous raffinate third mixture to step (a), characterized in that the concentration of caprolactam in second mixture is 5–35 wt. % and that the extraction agent used is an alkyl phenol having a boiling point which is higher than that of caprolactam.

2. Process according to claim 1, characterized in that step (a) is carried out at such a pressure that the system is in the liquid phase.

3. Process according to claim 1, characterized in that caprolactam is extracted with 5–100 vol. % of alkyl phenol relative to the amount of said second mixture.

4. Process according to claim 1, characterized in that extraction step (c) is carried out at a temperature of 50–220° C. and a pressure of 1–20 bar.

5. Process according to claim 1, characterized in that the boiling point of the alkyl phenol is more than 15° C. higher than the boiling point of caprolactam at 1.3 kPa (10 mm Hg).

6. Process according to claim 1, characterized in that the alkyl component of the alkyl phenol contains 6–25 carbon atoms.

7. Process according to claim 6, characterized in that the alkyl component of the alkyl phenol contains 9–15 carbon atoms.

8. Process according to claim 6 or 7, characterized in that the alkyl phenol used is dodecyl phenol, octyl phenol, nonyl phenol, n-hexyl phenol, 2,4-diisobutyl phenol, 2-methyl-4,6-di-tert-butyl phenol, 3-ethyl-4,6-di-tert-butyl phenol, 2,4,6-tri-tert-butyl phenol, or a mixture thereof.

9. Process according to claim 1, characterized in that the distillation in said recovery step (d) is a distillation of caprolactam, water and light components out of the organic phase to yield a fifth mixture comprising caprolactams, said fifth mixture being subjected to (i) ion exchange and hydrogenation, or hydrogenation and ion exchange and subsequently
(ii) distilling out the light components and
(iii) finally recovering caprolactam by distillation.

10. Process according to claim 1, characterized in that the distillation in said recovery step (d) is a distillation of caprolactam, water and light components out of said organic phase to yield a fifth mixture comprising caprolactam, said fifth mixture being concentrated to effect crystallization of caprolactam and finally separating out the crystallized caprolactam.

* * * * *